(12) United States Patent
Cho et al.

(10) Patent No.: US 8,795,196 B2
(45) Date of Patent: *Aug. 5, 2014

(54) THREE-DIMENSIONAL MICRO SPIKE AND METHOD OF MANUFACTURING THE SAME

(75) Inventors: Dongil Cho, Seoul (KR); Ahra Lee, Daegu (KR); Seung-Joon Paik, Seoul (KR); Myoung-Jun Jeong, Seoul (KR); HyunMin Choi, Anyang-si (KR); Jung-Min Lim, Anyang-si (KR); Sunkil Park, Bucheon-si (KR); Kyo-In Koo, Kyunggi-do (KR); Jae Won Ban, Seoul (KR)

(73) Assignee: SNU R&DB Foundation, Seoul (KR)

( * ) Notice: Subject to any disclaimer, the term of this patent is extended or adjusted under 35 U.S.C. 154(b) by 2001 days.

This patent is subject to a terminal disclaimer.

(21) Appl. No.: 11/999,989

(22) Filed: Dec. 7, 2007

(65) Prior Publication Data

US 2008/0167576 A1    Jul. 10, 2008

Related U.S. Application Data

(63) Continuation-in-part of application No. 11/284,365, filed on Nov. 21, 2005, now abandoned.

(30) Foreign Application Priority Data

Feb. 7, 2005    (KR) ........................ 10-2005-0011392

(51) Int. Cl.
| | |
|---|---|
| *A61B 10/00* | (2006.01) |
| *A61B 10/06* | (2006.01) |
| *A61B 10/02* | (2006.01) |
| *A61B 17/20* | (2006.01) |
| *A61B 17/00* | (2006.01) |
| *A61B 10/04* | (2006.01) |

(52) U.S. Cl.
CPC .............. *A61B 10/06* (2013.01); *A61B 17/205* (2013.01); *A61B 10/0233* (2013.01); *A61B 2017/00345* (2013.01); *A61B 2014/320064* (2013.01); *A61B 2010/0225* (2013.01); *A61B 2010/045* (2013.01)
USPC ........................................................ 600/564

(58) Field of Classification Search
USPC .......................... 600/562–571; 606/151, 232
See application file for complete search history.

(56) References Cited

U.S. PATENT DOCUMENTS

| | | | | |
|---|---|---|---|---|
| 5,885,226 | A | * | 3/1999 | Rubinstein et al. ........... 600/564 |
| 5,928,161 | A | * | 7/1999 | Krulevitch et al. ........... 600/564 |

(Continued)

FOREIGN PATENT DOCUMENTS

| | | | | |
|---|---|---|---|---|
| JP | 2001-170058 | | 6/2001 | ............. A61B 10/00 |
| KR | 1020040034175 A | | 4/2002 | ............. H01L 31/12 |

*Primary Examiner* — Brian Szmal
*Assistant Examiner* — H. Q. Nguyen
(74) *Attorney, Agent, or Firm* — Head, Johnson & Kachigian, P.C.

(57) ABSTRACT

A micro spike having a three-dimensional structure made of single crystalline silicon and being capable of picking an enough amount of a tissue to examine the tissue while minimizing an examinee's pain with a minimal invasion when picking the tissue and a method of manufacturing the same are disclosed. The micro spike comprising: a main body part; extension parts inserted into a tissue when picking the tissue sample and integratedly extended from upper and lower parts of one side of the main body part; and a protrusion part integratedly protruded from at least one of side surfaces of the extension parts and inserted into the tissue to pick the tissue sample together with the extension parts when picking the living tissue sample.

25 Claims, 21 Drawing Sheets

(56) References Cited

U.S. PATENT DOCUMENTS

| | | | |
|---|---|---|---|
| 6,132,755 A | 10/2000 | Eicher et al. | A61F 2/14 |
| 6,264,617 B1 | 7/2001 | Bales et al. | A61B 10/00 |
| 6,379,324 B1 | 4/2002 | Bartstein et al. | A61B 17/20 |
| 7,374,530 B2 * | 5/2008 | Schaller | 600/16 |
| 8,118,753 B2 * | 2/2012 | Cho et al. | 600/562 |
| 2003/0065250 A1 * | 4/2003 | Chiel et al. | 600/115 |
| 2004/0087985 A1 * | 5/2004 | Loshakove et al. | 606/153 |
| 2007/0060837 A1 | 3/2007 | Dong, II et al. | |
| 2007/0219459 A1 * | 9/2007 | Cohen | 600/564 |

* cited by examiner

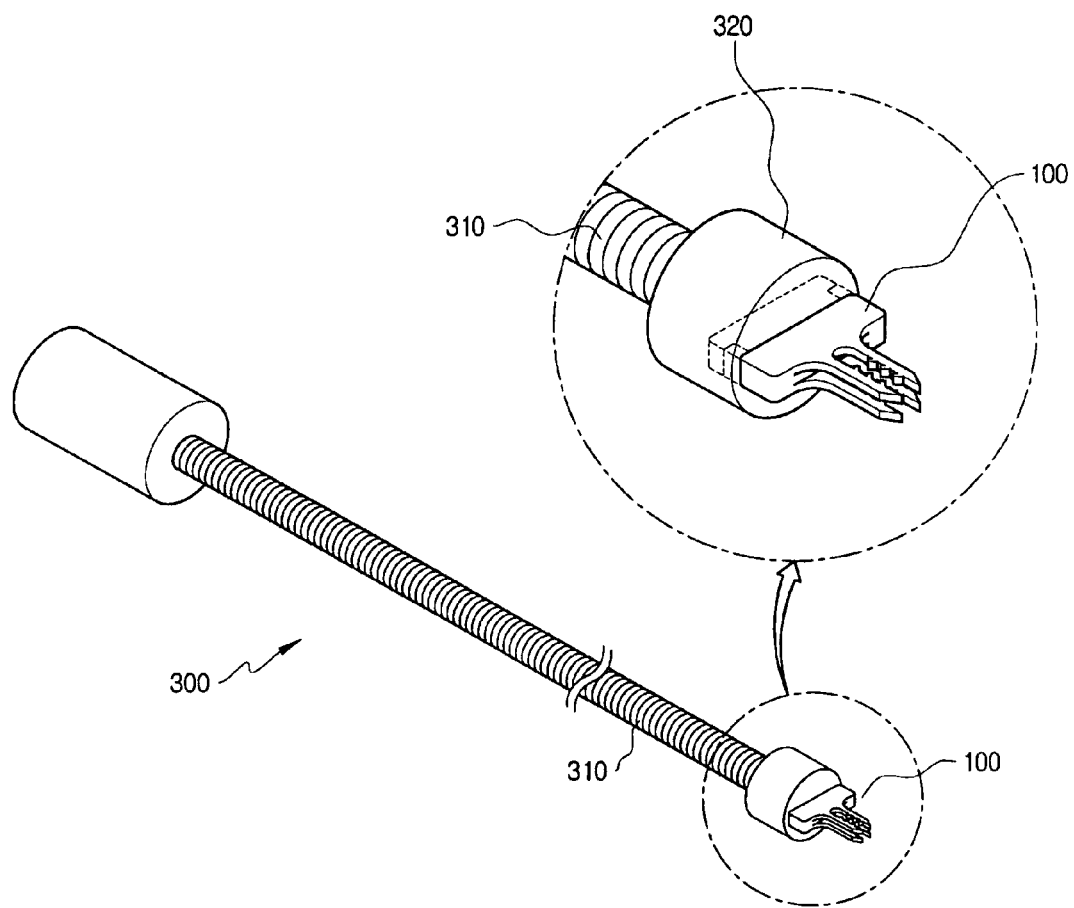

THREE-DIMENSIONAL MICRO SPIKE AND METHOD OF MANUFACTURING THE SAME

CROSS-REFERENCE TO RELATED APPLICATIONS

This application is a continuation-in-part application of U.S. patent application Ser. No. 11/284,365 filed Nov. 21, 2005, now abandoned, which claims priority to the Republic of Korea Patent Application No. 10-2005-0011392 filed Feb. 7, 2005.

BACKGROUND OF THE INVENTION

1. Field of the Invention

The present invention relates to a micro spike which is a biopsy tool used to pick a tissue, and more particularly to a micro spike having a three-dimensional structure made of a single crystalline silicon and being capable of picking an enough amount of a tissue to examine the tissue while minimizing an examinee's pain with a minimal invasion when picking the tissue, and a method of manufacturing the same.

2. Description of the Prior Art

In the medical area, biopsy tools are essential in preparing tissue samples for pathological tests. However, since a conventional biopsy tool according to the prior art has a relatively big size, an amount of the extracted tissue samples is unnecessarily much and it causes significant discomfort, risk, and injury to the patients. However, since a biopsy tool according to the prior art has a relatively big size, an amount of a tissue picked is unnecessarily much when picking the tissue. In addition, it is required many amounts of reagents to analyze the sampled tissue and the patient should endure pain and risk resulting from the medical treatment.

For solving the above problems, there are suggested micro biopsy/precision cutting devices having a relatively small size, which are made by applying a micro machining process and a precision process. However, since most of the micro biopsy tools or precision cutting devices having a small size have a complex structure, it is difficult to manipulate the device when performing the biopsy and thus a skillful operator is required.

FIG. 1 shows a catheter used to pick a tissue sample according to the prior art. As shown, the catheter comprises forceps jaws 202, a micro needle 204 and a main body 201.

The catheter 200 shown in FIG. 1 has a structure such that the micro needle 204 having an jagged structure is mounted to a center of the catheter and the forceps jaws 202 are mounted to both sides of the needle. The catheter 200 of FIG. 1 picks a tissue such a manner that a surface of the tissue is stretched when pricking and drawing the tissue 500 with the micro needle 204 and then the forceps jaws 202 pick up and separate the stretched tissue. The catheter has an advantage of securing an accurate picking amount when picking the tissue.

However, when picking the tissue using the catheter 200 of FIG. 1, since two processes of pricking the tissue with the micro needle 204, and picking and separating the tissue with the forceps jaws 202 should be performed, an examinee's pain is increased. In addition, there is an inconvenience that a movement of forceps jaws 202 should be manipulated to separate the tissue under state that the tissue is stretched with the micro needle 204.

Additionally, according to the catheter 200 shown in FIG. 1, since the main body 201, the micro needle 204 and the forceps jaws 202 are integrated, the main body part 201 as well as the micro needle 204 and the forceps jaws 202 should be discarded after the catheter 200 is once used for the tissue picking. In other words, since the prior catheter is disposable, it is not desirable from a point of view of an efficient use of resources.

In the mean time, there are known methods using a substrate bonding, a LIGA (Lithographic, Galvanoformung, Abformung) process, and a laser micro machining process for manufacturing a three-dimensional micro device. Hereinafter, each of the methods will be briefly described.

The substrate bonding method is such that a structure is respectively formed on two substrates and then the two substrates are bonded to form a three-dimensional structure at a last step. According to this method, it is difficult to bond the substrates and there is much possibility of the structure to be transformed due to stress between the two substrates.

The LIGA method is such that a photographing process is performed on a thick photoresist using an ion beam such as ultraviolet or X-ray emitting from a particle accelerator, a gap between the photoresist remaining after development is filled up by an electroplating method, and then a metal mold box for molding is formed.

A three-dimensional LIGA process is a method of manufacturing a three-dimensional structure by performing an exposure process while rotating the ion beam to several directions. This method has a disadvantage such that it is difficult to obtain equipment capable of exposing the ion beam since the equipment is very expensive. In addition, since the three-dimensional structure made according to the LIGA process is hard to plate a photoresist structure after the exposure, it is impossible to make the molding box. Further, since the biopsy devise of the three-dimensional structure consisting of the photoresist material only has very low durability, it is impossible to virtually use it for the biopsy.

Since the laser micro machining method processes an arbitrary shape in a manner of scanning the shape with the laser so as to make the shape, it takes much time to manufacture it. In addition, since a manufacturing cost is high, there is a difficulty in the mass-production.

As described above, according to the prior methods of manufacturing the micro device, there are many difficulties such as a complex manufacturing process, a requirement of expensive manufacturing equipment, and a low durability of the micro device. Accordingly, there is a need of a method capable of manufacturing a three-dimensional biopsy tool having a firm structure while easily manufacturing it. In addition, as described above, there is needed a biopsy tool which is capable of minimizing a risk and a patient's pain when picking the tissue and which can be handled easily.

A technology concerning transcorneal drug-release system and a micropin is disclosed in U.S. Pat. No. 6,132,755. Said transcorneal drug-release system and micropin are devices for injecting the drug into the skin, manufactured by sintering in a mould (col. 4 lines 12-15). The device is attached or fixed onto the skin like plaster or a wristwatch and cannot be inserted into the body. Therefore, said transcorneal drug-release system only injects drug into the skin and make the drug penetrate the Stratum corneum. Said transcorneal drug-release system is unable to pick tissue of an organ in the body or inject drug into a specific organ in the body.

SUMMARY OF THE INVENTION

Accordingly, the present invention has been made to solve the above-mentioned problems occurring in the prior art. The object of the present invention is to provide a micro spike capable of picking an enough amount of a tissue to examine it through a simple process of inserting and extracting the device into and from the tissue and minimizing a patient's pain with a minimal invasion when picking the tissue.

Another object of the invention is to provide a method of manufacturing a micro spike having a firm structure with ease by applying a sacrificial bulk micromachining (SBM) processing method to a single crystalline silicon substrate.

In order to accomplish the object, there is provided a micro spike comprising a main body part made of single crystalline silicon and being insertion-mounted to a medical device for picking a living tissue sample; extension parts inserted into a tissue when picking the tissue sample and integratedly extended from upper and lower parts of one side of the main body part; and a protrusion part integratedly protruded from at least one of side surfaces of the extension parts and inserted into the tissue to pick the tissue sample together with the extension parts when picking the living tissue sample.

In addition, in order to accomplish the object, there is provided a method of manufacturing a three-dimensional micro spike comprising steps of forming an insulation film consisting of a stacked structure of silicon oxide film and silicon nitride film on both surfaces of a single crystalline silicon substrate, performing a photographing process on the insulation film, and thus forming a pattern of the insulation film, so as to define a shape of a micro spike; performing a first reactive ion etching process for the both surfaces of the single crystalline silicon substrate and thus etching the silicon substrate by a thickness of a extension part, so as to determine the thickness of the extension part; vapor-depositing a passivation film on each side surface of the part etched through the reactive ion etching process; performing a second reactive ion etching process for a region except the deposition part of the passivation film so as to define a sacrificial layer; performing an anisotropic wet etching for the silicon substrate etched through the second reactive ion etching process using a basic solution; and performing a dicing process so as to separate the micro spike from the wet-etched silicon substrate.

BRIEF DESCRIPTION OF THE DRAWINGS

The above and other objects, features and advantages of the present invention will be more apparent from the following detailed description taken in conjunction with the accompanying drawings, in which:

FIG. 3A illustrates an example of a micro spike attached to a medical device;

DETAILED DESCRIPTION OF THE PREFERRED EMBODIMENTS

Hereinafter, preferred embodiments of the present invention will be described with reference to the accompanying drawings. In the following description of the present invention, a detailed description of known functions and configurations incorporated herein will be omitted when it may make the subject matter of the present invention rather unclear.

Figure 1:
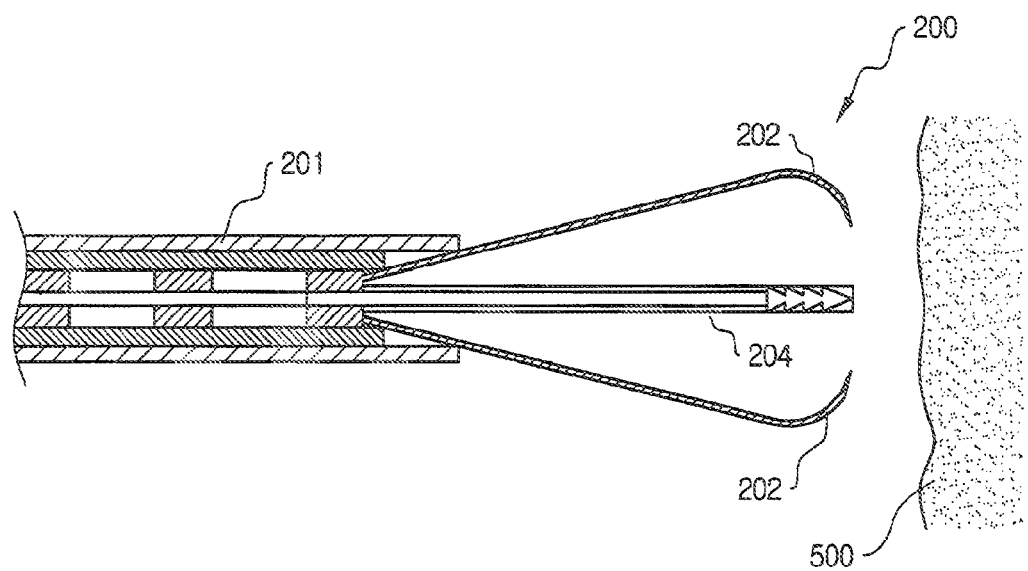
FIG. 1 shows a micro needle used to pick a tissue sample according to the prior art.
Figure 2A:
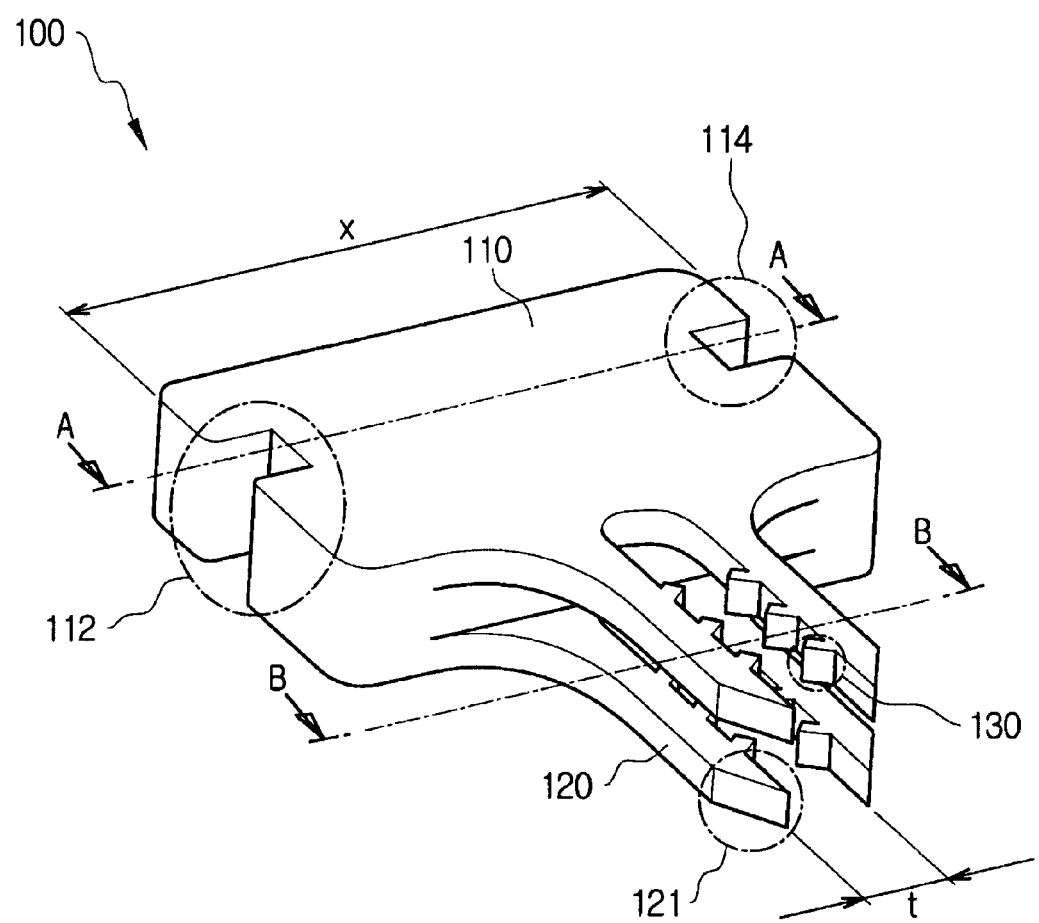
FIG. 2A is a perspective view of an external structure of a micro spike according to an embodiment of the invention.
Figure 2B:
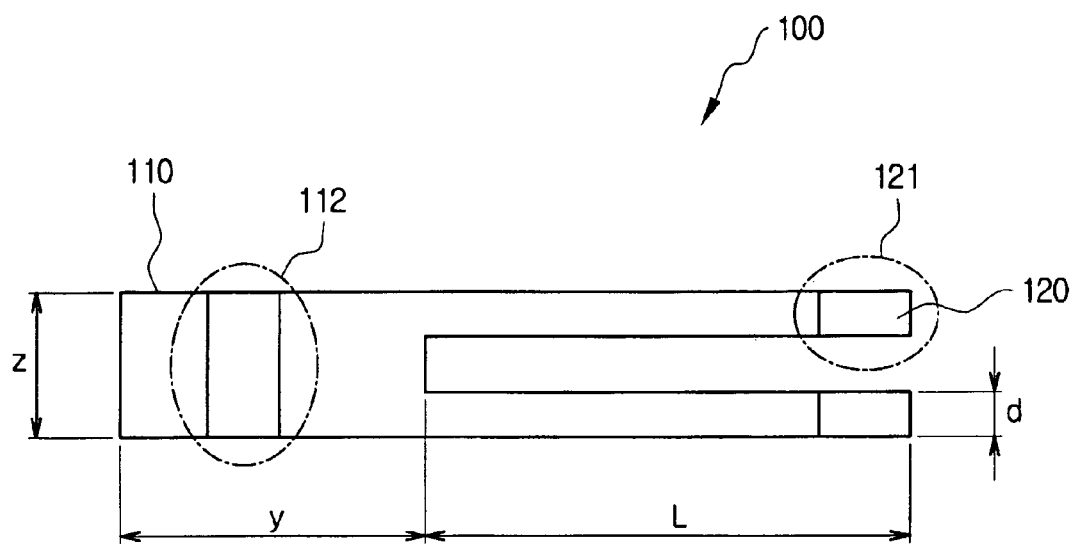
FIG. 2B is a side view of a micro spike according to an embodiment of the invention.

FIG. 2A shows an external structure of a micro spike according to an embodiment of the invention. FIG. 2 is a side view of said micro spike. As shown in FIG. 2A, the micro spike 100 according to an embodiment of the invention may comprise a main body part 110, an extension part 120 and a protrusion part 130. In addition, the micro spike may be embodied in one united body integrated with the main body part 110, the extension part 120 and the protrusion part 130 and made of single crystalline silicon.

The main body part 110 comprises a connection means that is structured to easily connect with a mount device, for example, a medical device such as an endoscope, capsule-type endoscope, catheter, tweezers or a pincette. For instance, the micro spike 100 according to the invention can be easily connected and separated to and from an existing medical device just by forming a connection means, such as a recess 112, 114 in the existing medical device into which the main body part 110 can be inserted.

FIG. 3A illustrates an example of the way in which a micro spike 100 according to the invention is attached to a medical device 300 such as a catheter. A micro spike 100 according to the invention is attached to the end part 320 of the wire 310 of said medical device 300, and the wire 310 of said medical device 300 is inserted into the body. For example, it is inserted into the body by piercing the skin or inserted into the esophagus or the intestine like an endoscope and close to the organ (e.g., stomach, liver, intestine, etc.) in the body.

Afterwards, said micro spike 100 attached to the end part 320 of said wire 310 is inserted into the organ to be examined, and when the wire 310 of said medical device 300 is taken out of the body, the tissue picked by said micro spike 100 is also taken out of the body. In sum, the tissue of an organ in the body can be picked by inserting a micro spike 100 into the body along with the wire 310 of a medical device 300 and taking them out of the body.

Figure 3B:
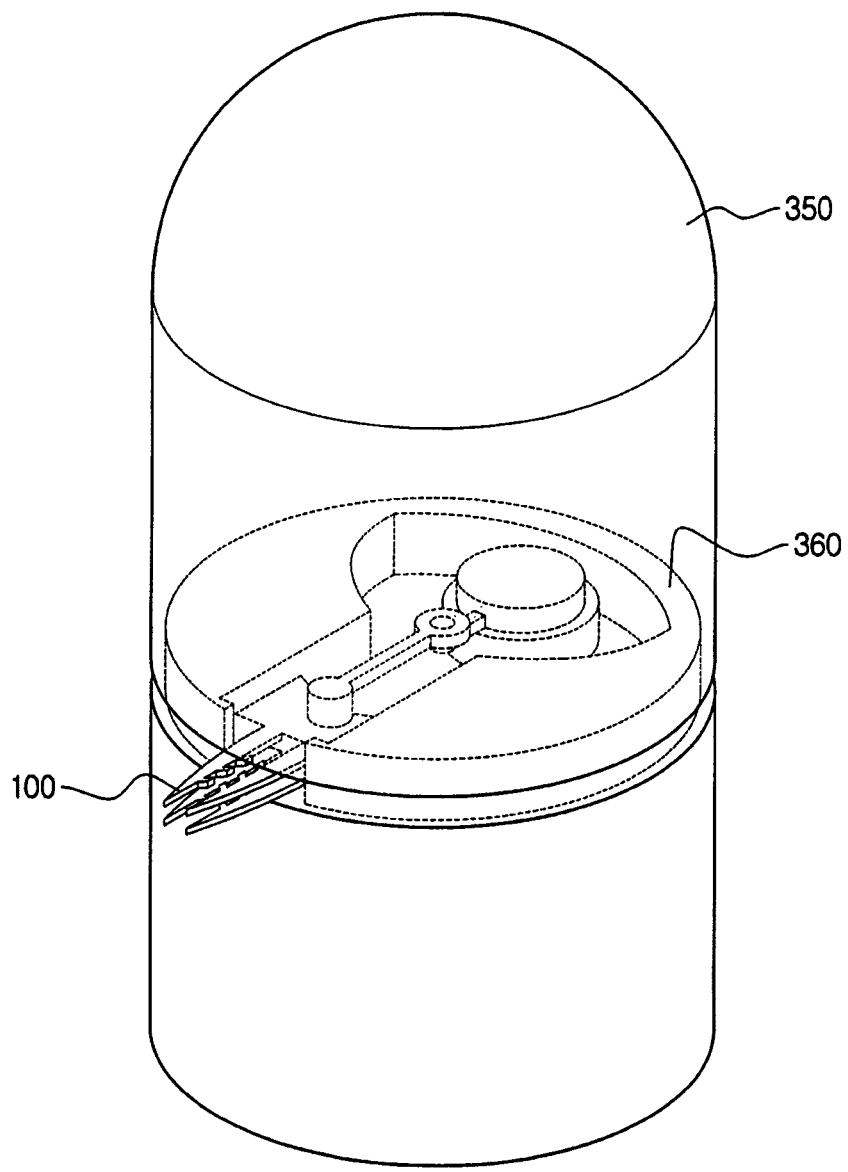
FIG. 3B illustrates another example of a micro spike attached to a medical device.

FIG. 3B illustrates an example of the way in which a micro spike 100 according to the invention is attached to a capsular endoscope 350. A micro spike 100 according to the invention is attached to the actuator 360 of said capsular endoscope 350, and the capsular endoscope 350 is inserted or taken into the body. For example, the capsular endoscope 350 may be swallowed and pass the esophagus and the gastrointestinal.

Figure 3C:
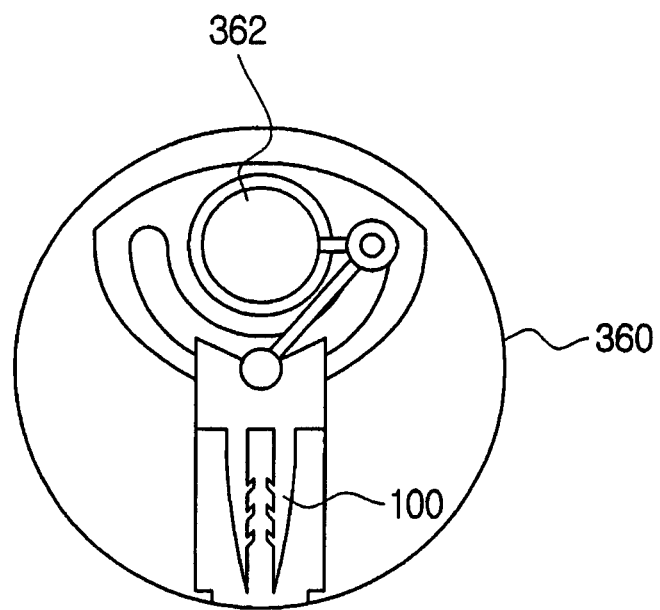
FIGS. 3C and 3D illustrate an example of operation of the micro spike depicted in FIG. 3B.
Figure 3D:
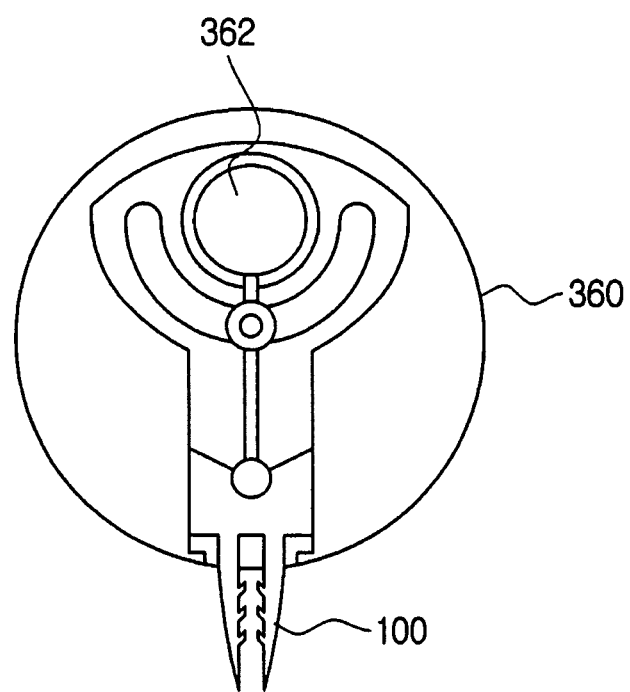

FIGS. 3C and 3D illustrate an example of operation of the micro spike depicted in FIG. 3B. As shown in FIG. 3C, the micro spike 100 is located in the internal of the capsular endoscope 350. When the capsular endoscope 350 is arrived at an organ whose tissue is to be examined, the extension part of the micro spike 100 comes out of the capsular endoscope 350 by rotating the rotor 362 which is equipped in the actuator 360 of the capsular endoscope 350 and connected with the main body part of the micro spike 100 as shown in FIG. 3D. Then, the extension part of the micro spike 100 is inserted into the organ to be examined, and when the extension part of the micro spike 100 is taken out of the organ, the tissue of the organ may be picked. When the rotor 362 is further rotated, the extension part of the micro spike 100 and the picked tissue come into the internal of the capsular endoscope 350.

Referring again to FIG. 2A, FIG. 2A shows at least one extension part 120 is respectively formed at an upper part and a lower part of one side of the main body part 110. Regarding the number of the extension part 120, two extension parts are respectively formed at the upper part and the lower part of one side of the main body part 110 in the embodiment shown in FIG. 2. However, it should be noted that the number of the extension part may be variously adjusted as necessary. For example, it is possible to provide three or more extension parts when more amounts of tissue samples are required. Preferably, the number of the extension parts provided to the upper and lower parts of the one side of the main body part 110 may be from 1 to 10.

Figure 4:
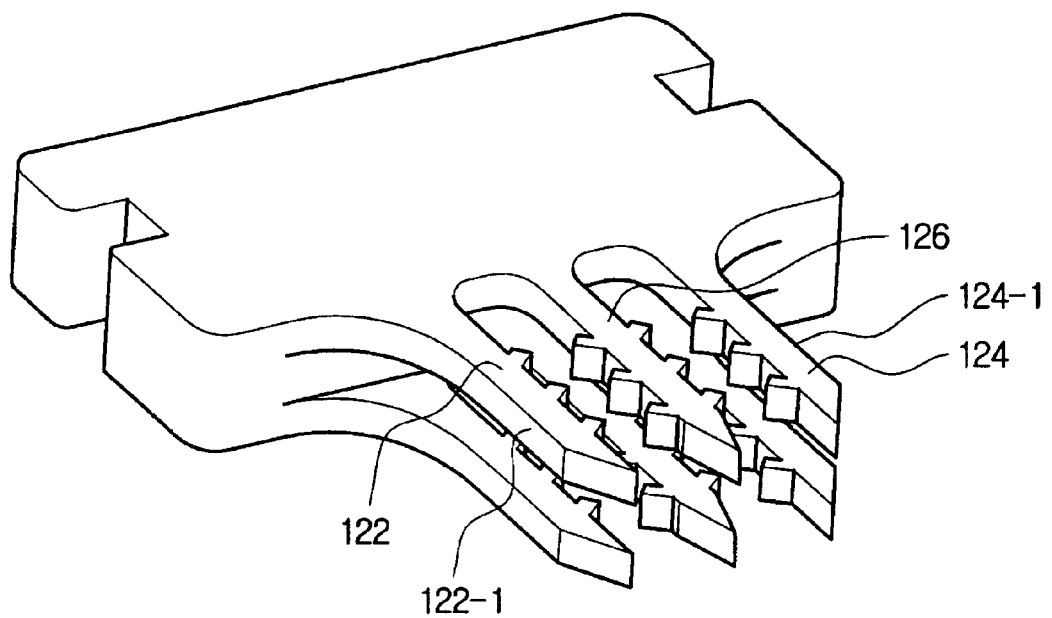
FIG. 4 is a perspective view of another embodiment of a micro spike according to the invention, wherein extension parts are further formed in the center.

Furthermore, in the embodiment in FIG. 2A, two extension parts 120 are respectively formed by extending from the left and right part of the main body part 110. However, the extension part may be formed by extending from the center part between the left side and the right side as necessary. Therefore, FIG. 4 illustrates an example of a micro spike wherein an extension part 126 is formed in the center part between the left part and the right part, as well as the extension part 122 on the left part and the extension part 124 on the right part of the main body part 110.

When performing a biopsy using the micro spike according to the invention, it is the extension part 120 that is inserted into the organ from which tissue is to be picked. Accordingly, as illustrated in FIG. 2A, a leading portion 121 of the extension part 120 is preferably formed so that it is easily inserted into the bio tissue. For example, the leading portion is preferably shaped into a pointed form.

In the mean time, considering a characteristic of a device being inserted into a living body, a size thereof is preferably limited within a predetermined range. From this point of view, it is preferred that a length (L in FIG. 2B) of the extension part 120 is within a range of 1.5 mm~15 mm (more preferably, 2 mm~10 mm), and an interval (t in FIG. 2A) between the extension parts 120 is within a range of 5 μm (micrometer)~30 mm (more preferably, 100 μm~5 mm). Further, it is preferred that the width (k in FIG. 5) of said extension part 120 is within a range of 10 μm~10 mm (more preferably, 100 μm~1 mm). Further, it is also preferred that the thickness (d in FIG. 2B) of said extension part 120 is within a range of 10 μm~10 mm (more preferably, 100 μm~1 mm).

Further, the main body part 110 of a micro spike 100 according to the invention is also inserted into the body by a medical device, and therefore, it is preferable that the size of said main body part 110 be limited to a certain range. For instance, it is preferred that the width (x in FIG. 2A) be within the range of 100 μm~50 mm (more preferably 1 mm~5 mm). It is preferred that the length (y in FIG. 2B) of said main body part 110 also be limited to 100 μm~50 mm (more preferably 500 μm~5 mm). It is preferred that the thickness (z in FIG. 2B) of said main body part 110 be limited to 100 μm~10 mm (more preferably 200 μm~2 mm).

The protrusion part 130 serves to induce a separation of the tissue and to fix the separated tissue when picking the tissue. The protrusion part 130 may be formed at a side of the extension part 120 at an interval. It is preferred that said protrusion part 130 be formed on the side surfaces of said extension part 120, which are opposite to each other as shown in FIG. 2A or FIG. 4. For example, a protrusion part 130 is not formed on the outer side surfaces (122-1, 124-1) of an extension part 122 on the left part and an extension part 124 on the right part of the micro spike shown in FIG. 4. It is also preferred that a protrusions part 130 be formed on both side surfaces of the extension part 126 which are formed at the center 126 as shown in FIG. 4.

Regarding the number of the protrusion part 130, three protrusion parts are formed on each extension part 120 in FIG. 2A. However, it should be noted that more or less than three protrusion parts may be provided as necessary.

Regarding a shape of the protrusion part 130, the protrusion part 130 shown in FIG. 2A has a wing shape inclined in a forward direction for a longitudinal direction of the extension part toward the leading portion 121. If picking the tissue sample through the micro spike 100 having the above wing-shaped protrusion part 130, it is possible to easily pick the tissue sample since the tissue is caught by the wing-shaped protrusion part 130 and taken off together with it when inserting and extracting the extension part 120 into and from the target tissue.

Figure 5:
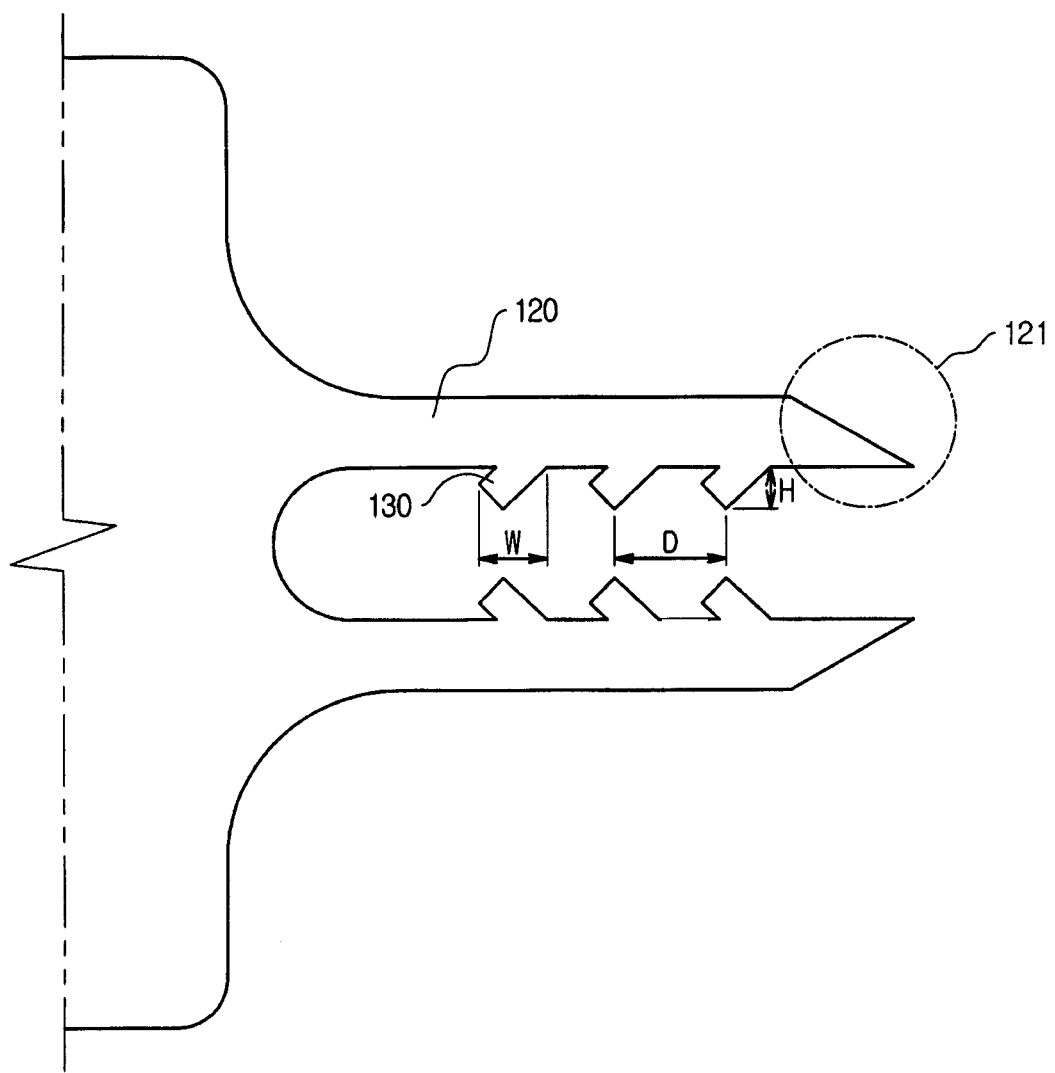
FIG. 5 shows an extension part and a protrusion part of the micro spike according to an embodiment of the invention in detail.

FIG. 5 shows the extension part 120 and the protrusion part 130 of the micro spike according to an embodiment of the invention in detail. Regarding a size of the protrusion part, it is preferred that a width (W) of the protrusion part 130, a space (D) between the protrusion parts and a height (H) of the protrusion part are set to be within a range of 5 μm~5 mm (more preferably, 50 μm~1 mm), considering the characteristic of the device being inserted into the living body.

Figure 6:
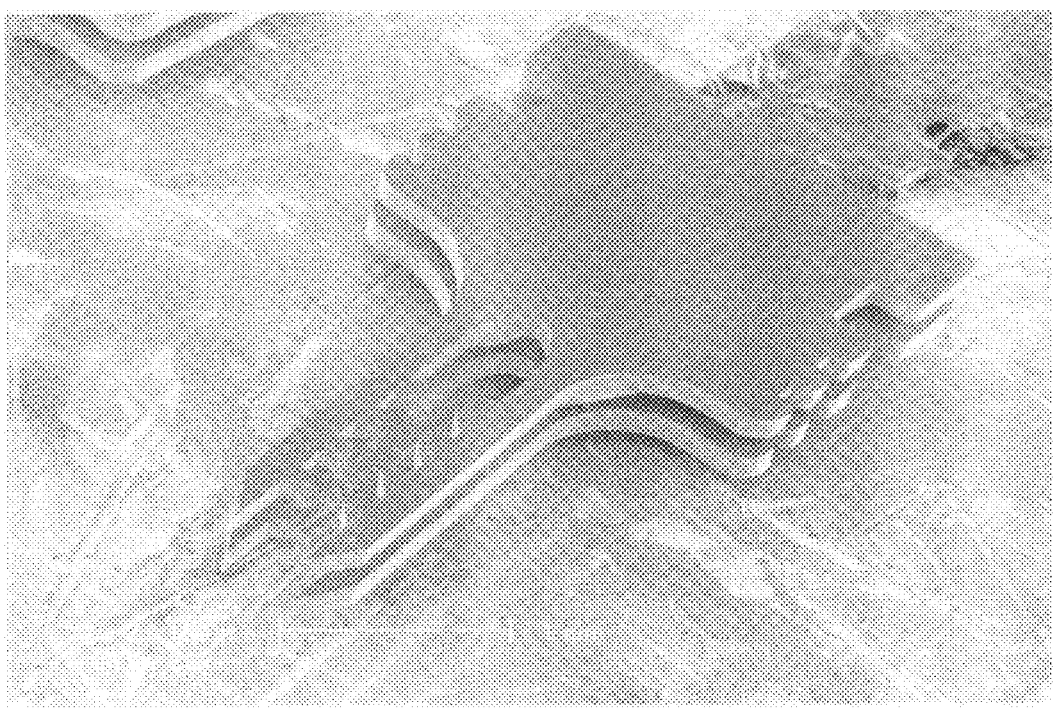
FIG. 6 is an electron microscopic photograph of a micro spike formed with a wing-shaped protrusion part according to an embodiment of the invention.

FIG. 6 is an electron microscopic photograph of a micro spike formed with the wing-shaped protrusion part 130 according to an embodiment of the invention. In the photograph of FIG. 6, it can be seen that two extension parts are respectively provided to the upper and lower parts of the main body part and four protrusion parts are respectively formed on the side surfaces, which are opposite to each other, of each extension parts. A protrusion part is not formed on the outer side surfaces of said extension part. By not forming a protrusion part on the outer side surface of an extension part, the friction caused by the penetration of a micro spike into an organ is minimized, as well as the examinee's pain.

Figure 7:
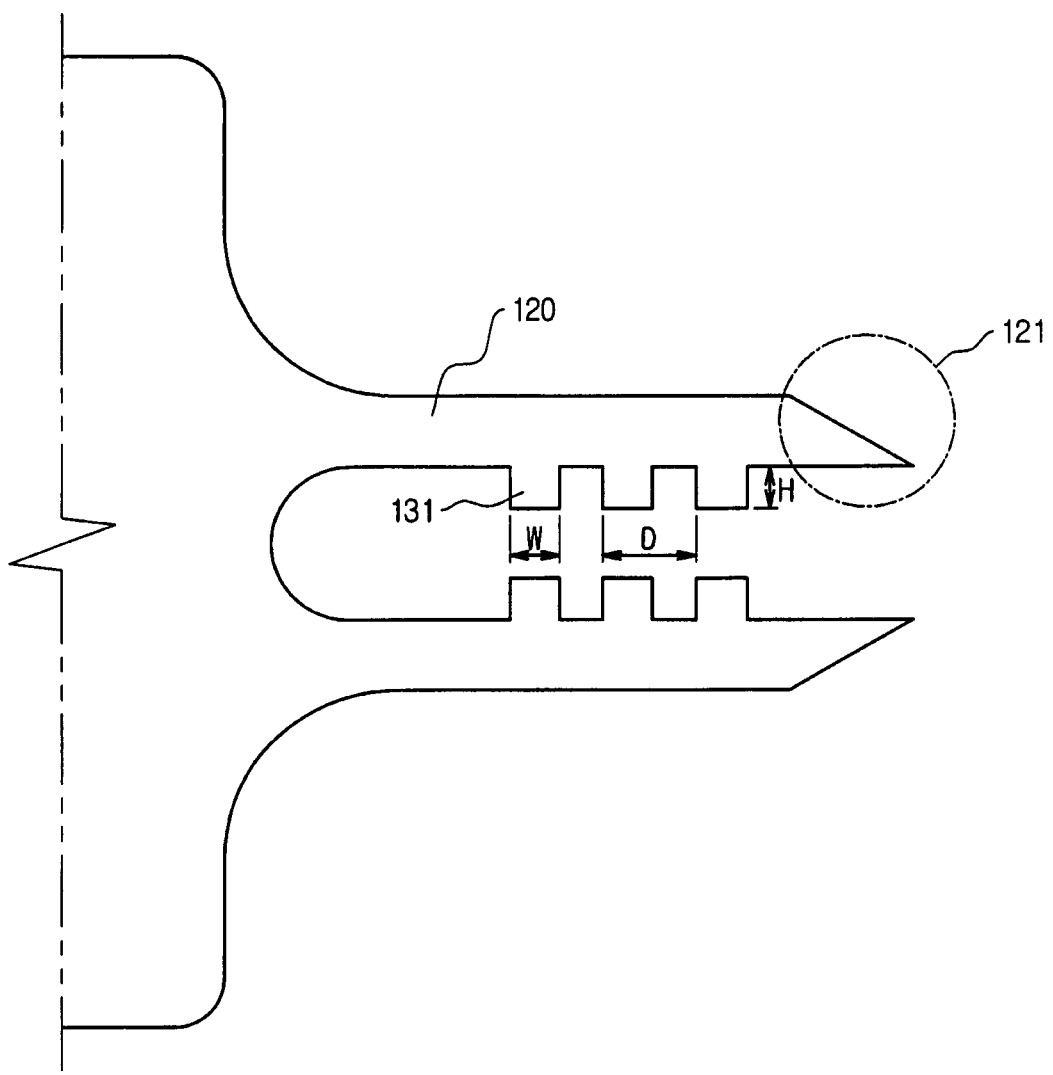
FIG. 7 illustrates a micro spike having a rectangular protrusion part according to an embodiment of the invention.

FIG. 7 illustrates a micro spike having a rectangular protrusion part according to an embodiment of the invention. Regarding the protrusion part 131 having a rectangular shape shown in FIG. 7, the various number of the protrusion parts can be formed as necessary, the protrusion part may be formed at side surfaces of the extension part which are opposite to each other, and ranges of a width (W) of the protrusion part, a space (D) between the protrusion parts and a height (H) of the protrusion part are same as the wing-shaped protrusion part 130 described above.

Figure 8:
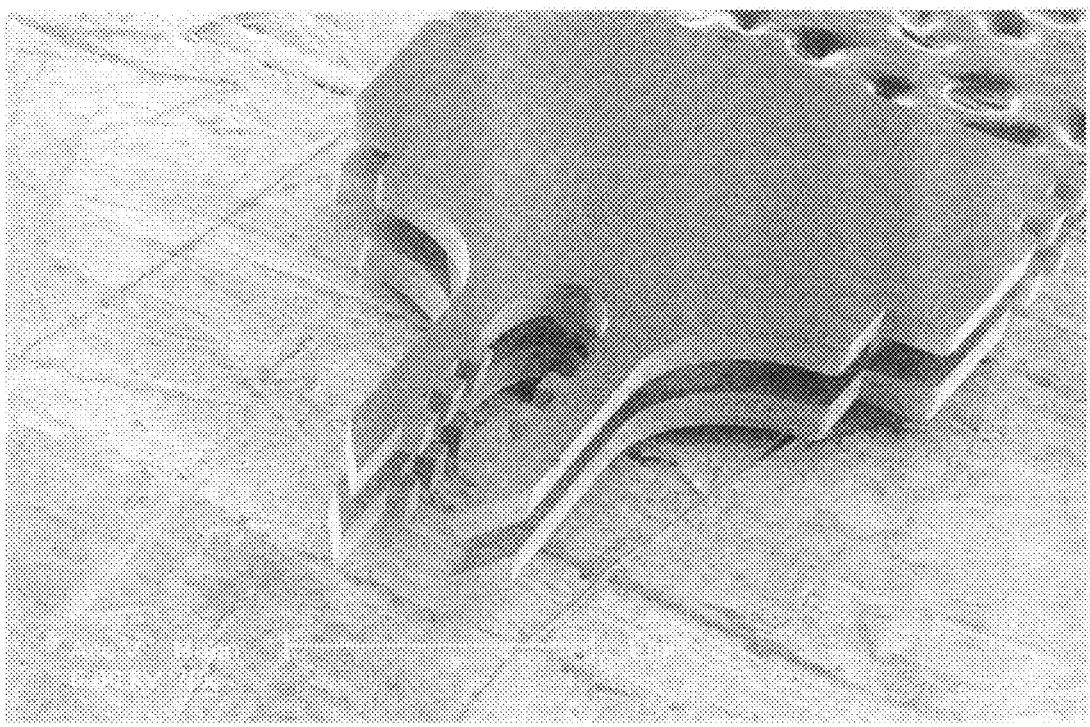
FIG. 8 is an electron microscopic photograph of a micro spike formed with a rectangular protrusion part according to an embodiment of the invention.

FIG. 8 is an electron microscopic photograph of a micro spike formed with the rectangular protrusion part 131 according to an embodiment of the invention. In the photograph of FIG. 8, it can be seen that two extension parts are respectively formed at the upper and lower parts of the main body part and three rectangular protrusion parts are respectively formed on side surfaces, which are opposite to each other, of each the extension parts.

Figure 9A:
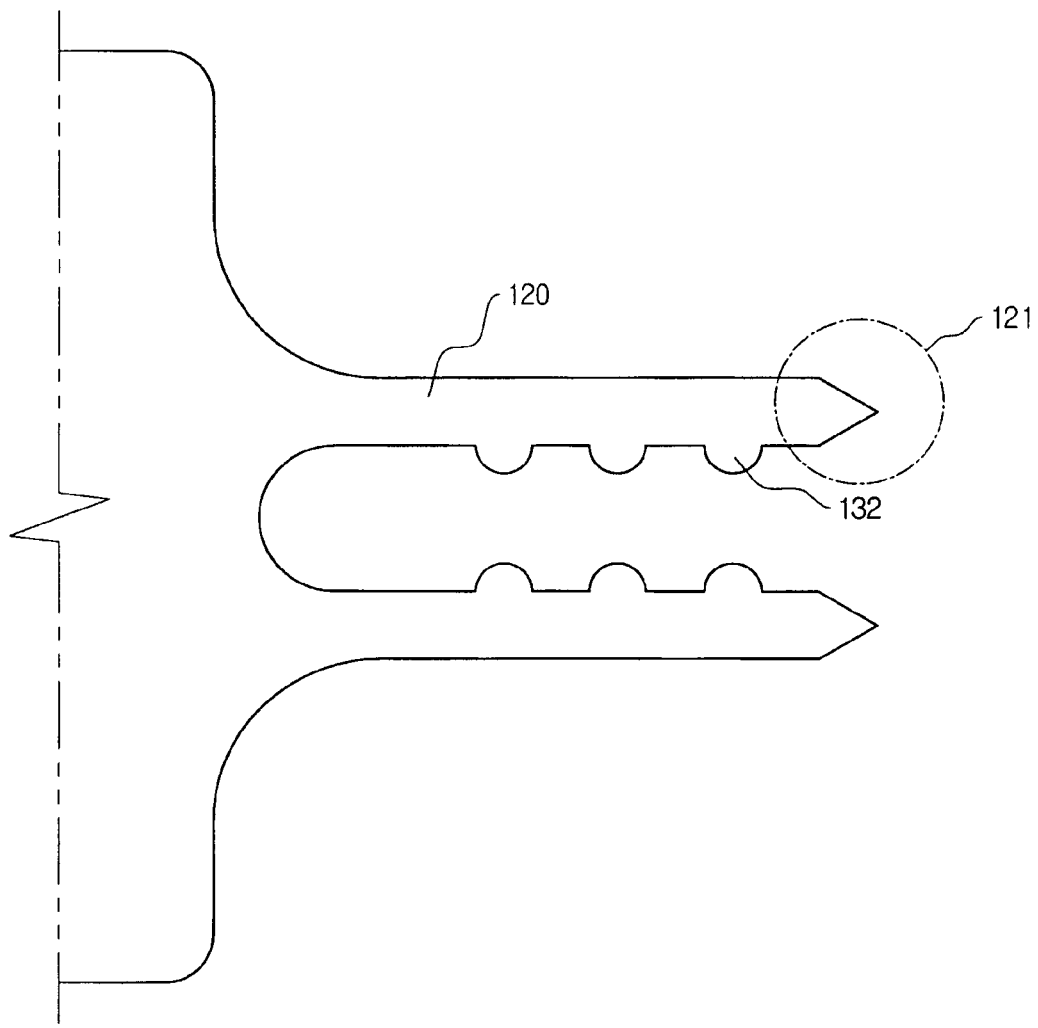
FIG. 9A shows a micro spike formed with a semicircular protrusion part according to an embodiment of the invention.
Figure 9B:
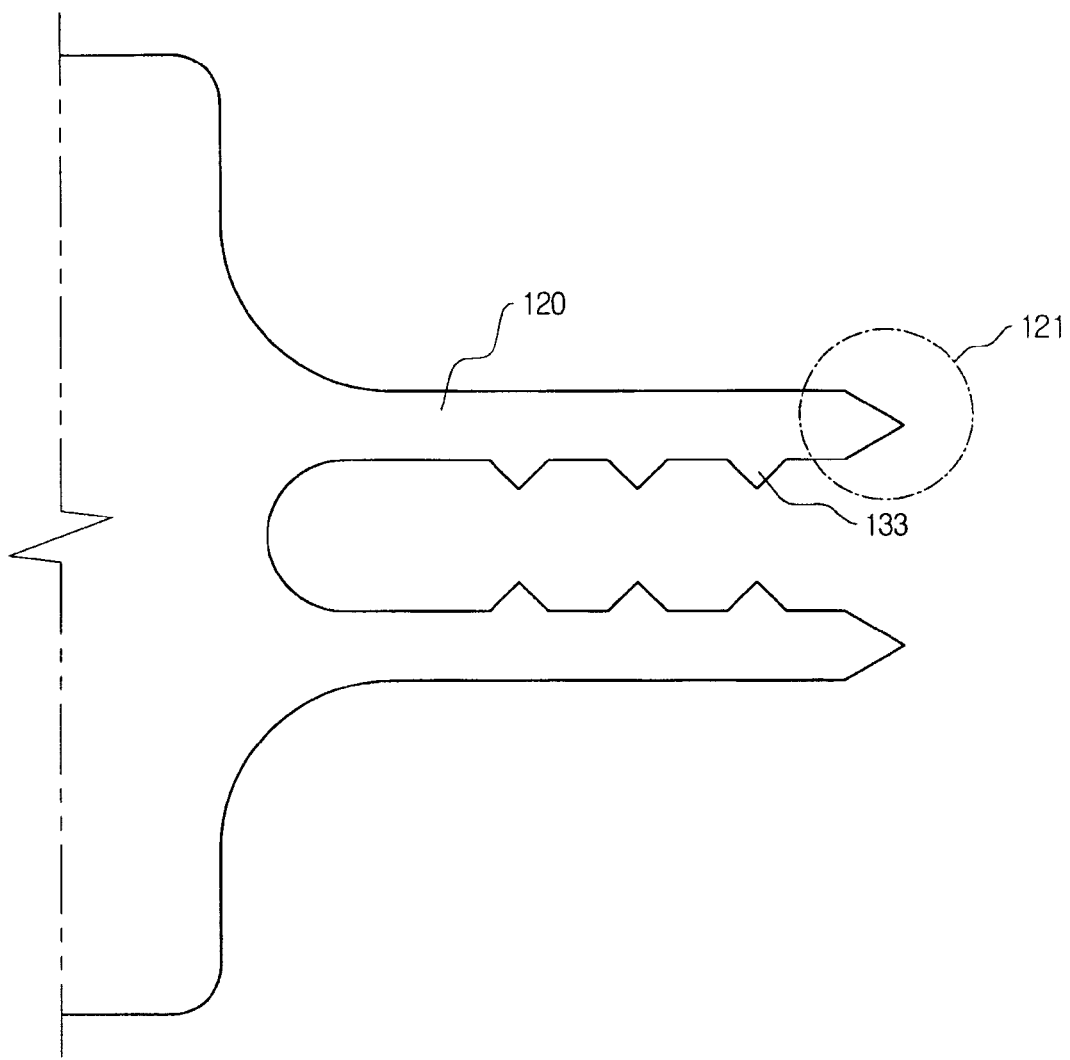
FIG. 9B shows a micro spike formed with a triangular protrusion part according to an embodiment of the invention.

Besides the wing shape and the rectangular shape described above, various shapes may be adopted for the protrusion part. For example, as shown in FIGS. 9A and 9B, a semicircular protrusion part 132 and a triangular protrusion part 133 may be provided. A size, a space and the number of the protrusion part are same as the wing-shaped or rectangular protrusion part. FIG. 9A shows a micro spike formed with a semicircular protrusion part according to an embodiment of the invention and FIG. 9B shows a micro spike formed with a triangular protrusion part according to an embodiment of the invention.

Figure 9C:
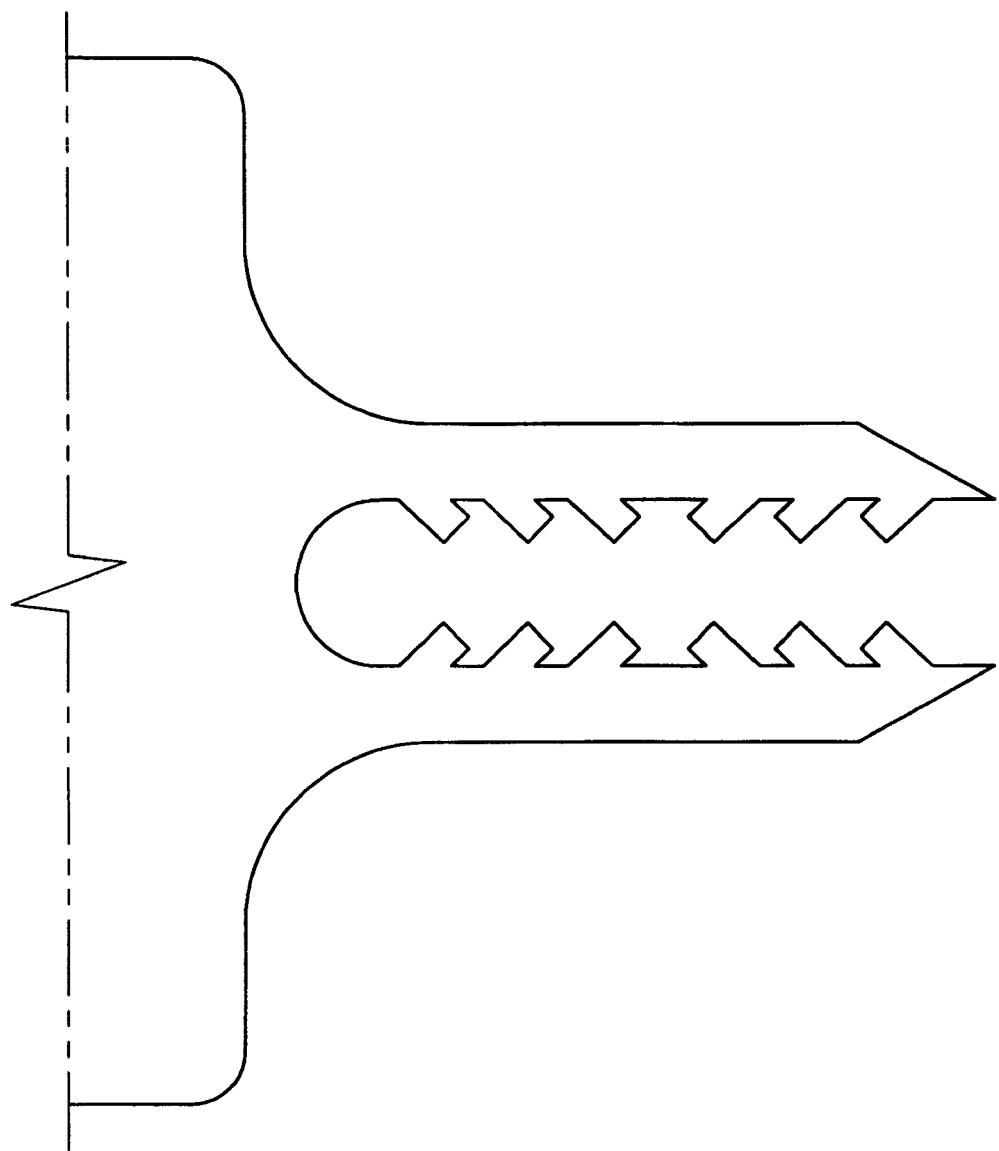
FIG. 9C shows a micro spike formed with both a forward-directed protrusion part and a reverse-directed protrusion part.

Further, said protrusion part may consist together of forward direction and reverse direction protrusion parts as shown in FIG. 9C.

Figure 10A:
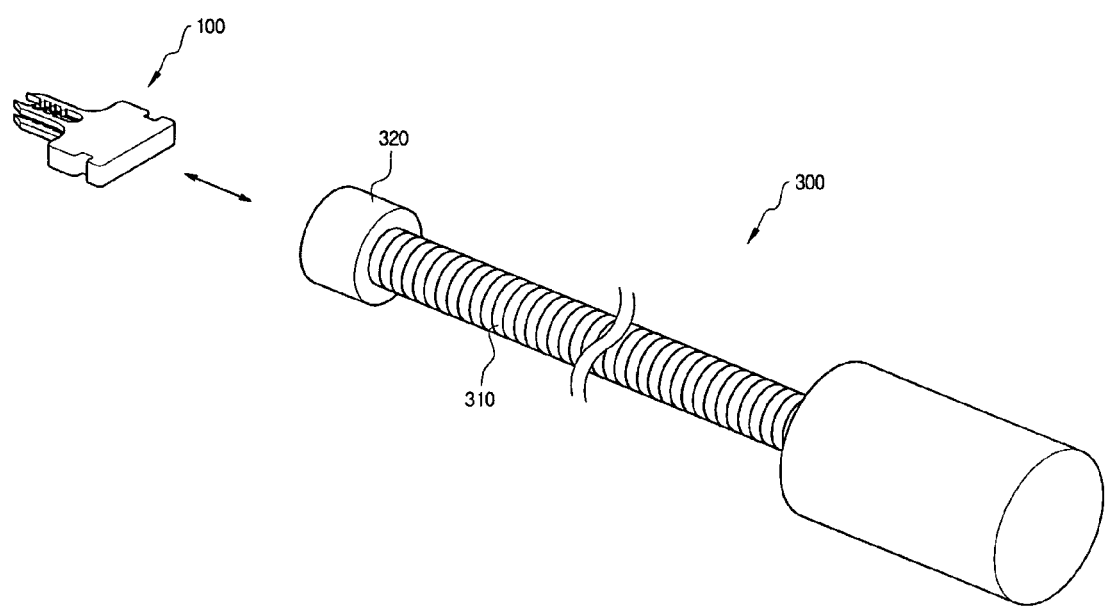
FIGS. 10A to 10D illustrate an example of a picking of a tissue sample using a micro spike of the invention.
Figure 10B:
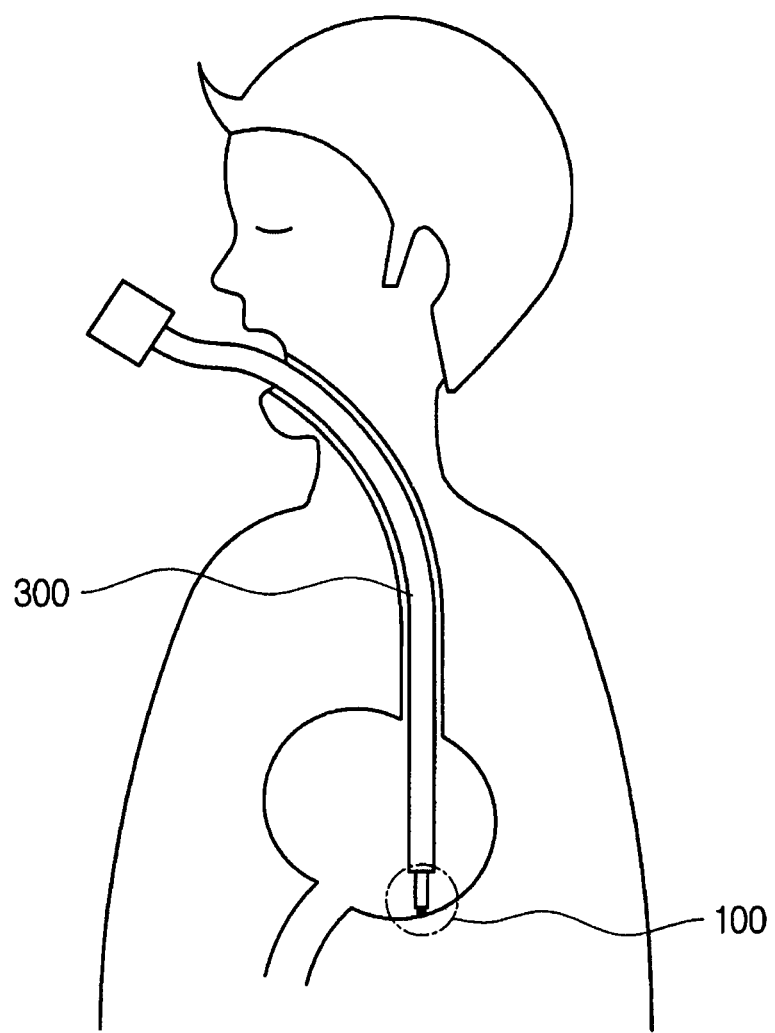
Figure 10C:
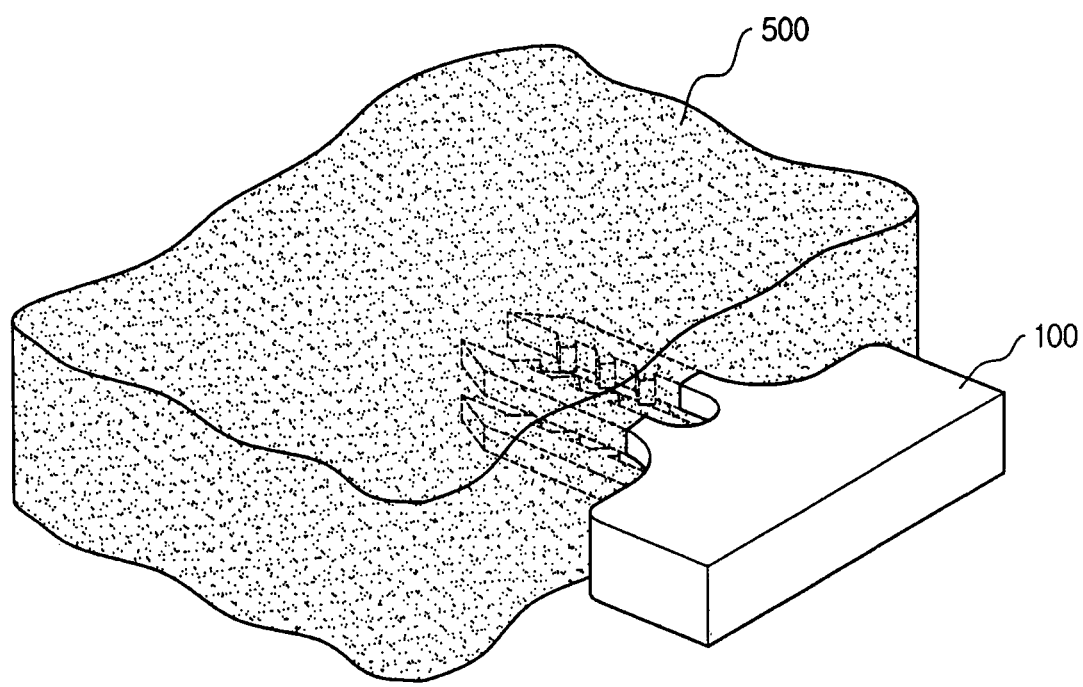

FIGS. 10A to 10C illustrate an example of a picking of a tissue sample using a micro spike of the invention. According to the invention, it is possible to easily pick the tissue just by inserting and extracting the extension part 120 of the micro spike into and from a tissue region from which a sample is picked. A procedure thereof will be more specifically explained in detail.

Firstly, a micro spike 100 according to the invention is attached to the end part 320 of a wire 310 of a medical device 300 such as an endoscope, as shown in FIG. 10A.

Figure 10D:
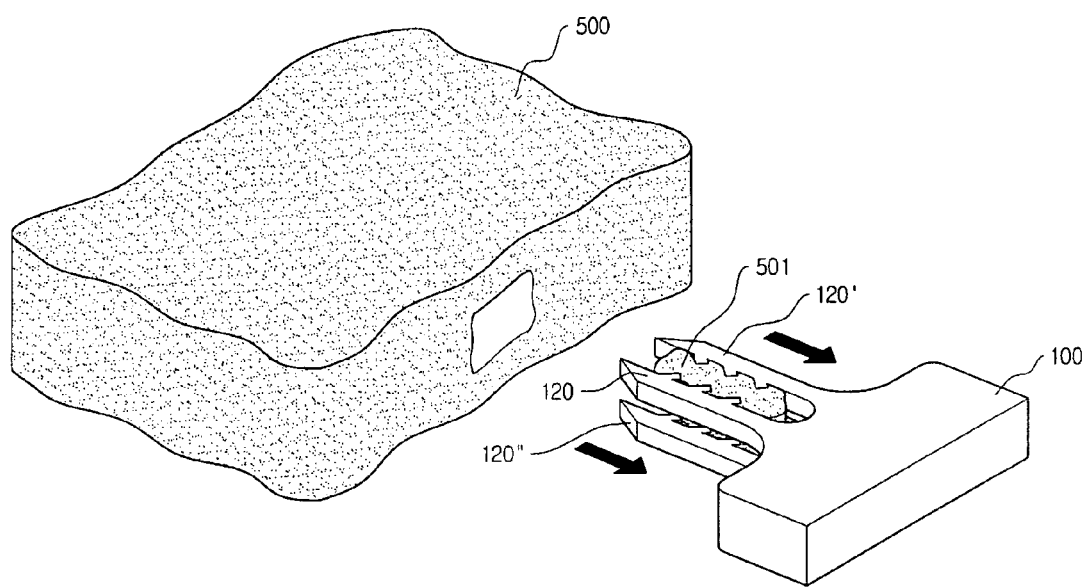

Then, a medical device 300 on which the micro spike according to the invention is attached is inserted into a body to pick the tissue of an organ in the body as shown in FIG. 10B. Then, the extension part 120 of the micro spike 100 attached to the medical device (not shown) is inserted into a tissue region 500 where the pathological examination is to be conducted. After inserting the extension part 120, when the extension part is extracted from the tissue region 500 by drawing the micro spike 100, the tissue sample 501 is caught by the protrusion part 130 formed on the side surface of the extension part 120 and taken off together with it as shown in FIG. 10D. In addition, since the micro spike of the invention comprises the extension parts 120 provided to both the upper and lower parts of the side surface of the main body part 110, when the inserted extension parts 120 are extracted from the tissue, the tissue is caught between the upper and lower extension parts as well as between the horizontal extension parts and taken off together with them. Accordingly, it is possible to pick an enough amount of tissue sample to examine the tissue just by inserting and extracting the extension parts 120 of the micro spike into and from the tissue region.

FIG. 10C shows the tissue sample 501 caught between the upper and lower extension parts when removing the three-dimensional micro spike of the invention from the tissue. As shown in FIG. 8B, since the micro spike of the invention is extracted together with the tissue sample caught between the right and left extension parts 120, 120' and between the upper and lower extension parts 120, 120", it is possible to pick an enough amount of the tissue sample to examine the tissue.

Figure 11:
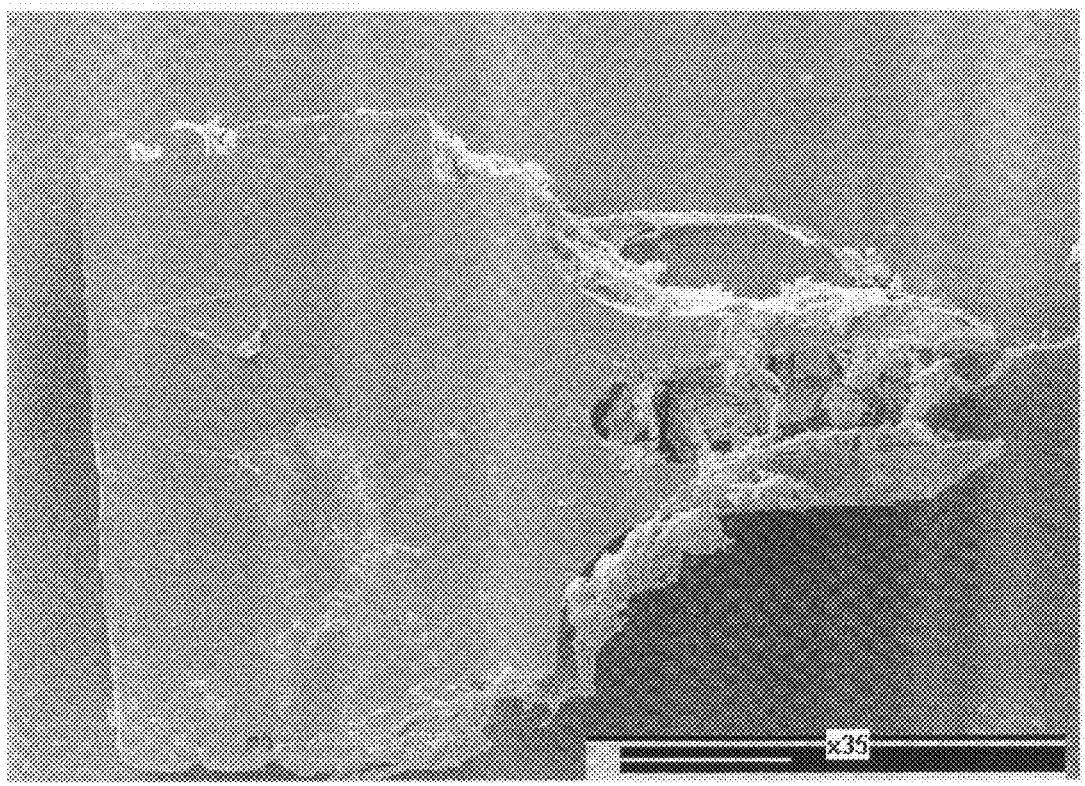
FIG. 11 is an electron microscopic photograph of a micro spike having a tissue sample picked according to an embodiment of the invention.

FIG. 11 is an electron microscopic photograph of a micro spike having a tissue sample picked according to an embodiment of the invention. In the photograph of FIG. 11, it can be seen that the tissue samples are evenly attached between the right and left extension parts or between the upper and lower extension parts of the micro spike. Such amount of tissue sample would be sufficient for conducting a pathological examination of the organ.

In the mean time, according to the micro spike of the invention, it is possible to coat a surface thereof with any material of a bio-compatible thin film such as a parylene thin film, a silicon oxide film, a silicon nitride film, gold and aluminum. Like this, it is possible to improve a bio-compatibility and strength of the micro spike by coating the surface of the micro spike with the above material.

As described above, when examining the living tissue with the three-dimensional micro spike of the invention, it is possible to pick the tissue sample simply by inserting and extracting the three-dimensional micro spike into and from the tissue. In addition, it is possible to relieve an examinee's pain and obtain a more amount of tissue sample, compared to the prior micro needle.

Hereinafter, a method of manufacturing a micro spike according to an embodiment of the invention will be described.

The micro spike of the invention can be manufactured by defining a shape of the micro spike on both surfaces of a single crystalline silicon substrate and then applying a sacrificial bulk micromachining (SBM) micro processing method. The silicon substrate is a material used for manufacturing a semiconductor integrated circuit or micro electromechanical systems (MEMS) and can be easily available. According to the both surfaces SBM micro processing technology, a three-dimensional structure having an arbitrary shape can be manufactured to have an arbitrary thickness and a three-dimensional micro structure can be manufactured through a simple procedure only, without a bonding process or special photographing process.

A shape and a thickness of the micro spike of the invention can be defined using a reactive ion etching method and an anisotropic wet etching method using a basic solution can be used to float the three-dimensional micro spike structure.

FIGS. 12A to 12D illustrate a process of manufacturing the micro spike according to an embodiment of the invention. For convenient explanations, a section of the main body part 110 taken along a line A-A in FIG. 2A will be described in conjunction with a section of the extension part 120 taken along a line B-B.

Figure 12A:
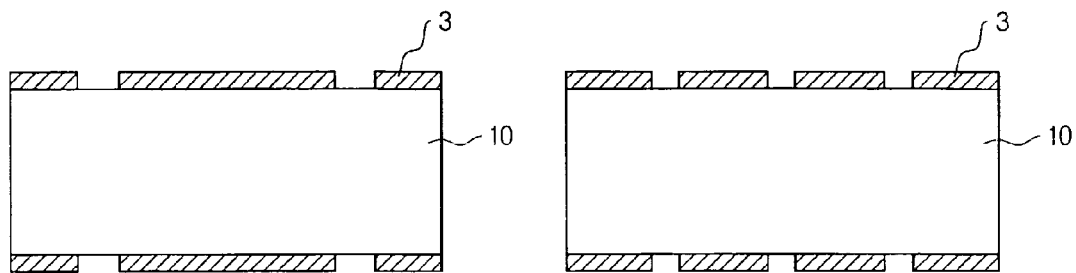
FIGS. 12A to 12D illustrate a process of manufacturing a micro spike according to an embodiment of the invention.

FIG. 12A illustrates a process for defining a shape of the main body part and the extension part 120 of the micro spike of the invention. As shown, a shape of the structure is defined on both surfaces of the silicon substrate 10 using photoresist and an insulation film 3, etc.

Specifically, the insulation film 3 for being used as an etching mask layer is formed on both surfaces of the single crystalline silicon substrate 10. For example, a silicon oxide film (not shown) is grown using a thermal oxidation, and then a low stress silicon nitride film (not shown) is deposited on the silicon oxide film using, for example, a low pressure chemical vapor deposition method, thereby forming an insulation film 3 consisting of the silicon oxide film and the silicon nitride film stacked. After forming the insulation film 3, a shape of both surfaces of the micro spike is defined using a photographing process. In other words, a photoresist film (not shown) is coated on the insulation film 3 as an etching mask layer of the insulation film, and then a photoresist layer on a region to be etched is selectively removed until the insulation film under the layer is exposed, thereby forming a pattern of the photoresist film on an insulation film region except the region to be etched. Then, an exposed portion of the insulation film 3 is etched using the pattern of the photoresist film as an etching mask layer until the silicon substrate 10 under the insulation film is exposed, thereby forming a pattern of the insulation film 3. Subsequently, the pattern of the photoresist film on the pattern of the insulation film 3 is completely removed, so that a shape of the micro spike is defined as shown in FIG. 12A.

Figure 12B:
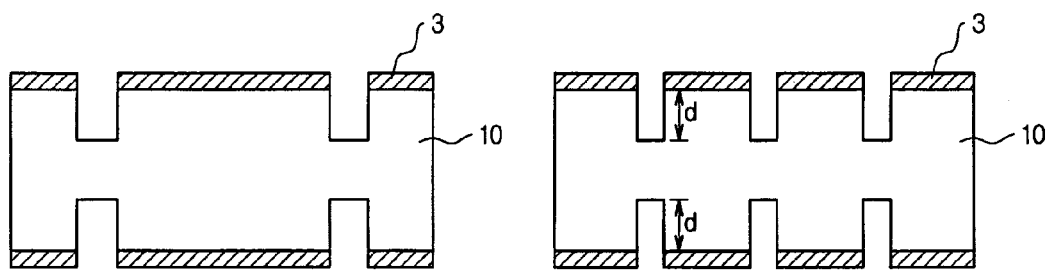

After defining the shape of the micro spike, the silicon substrate 10 is etched by a desired thickness through a reactive ion etching method using the pattern of the insulation film as an etching mask layer, so that a thickness (d) of the extension part of the micro spike is determined, as shown in FIG. 12B. At this time, the silicon substrate 10 is vertically etched as shown in FIG. 12B, and an etched depth can be easily regulated by the reactive ion etching method. In FIG. 12B, an etched depth of the silicon substrate 10 becomes a thickness of each extension part in a completed micro spike.

Figure 12C:
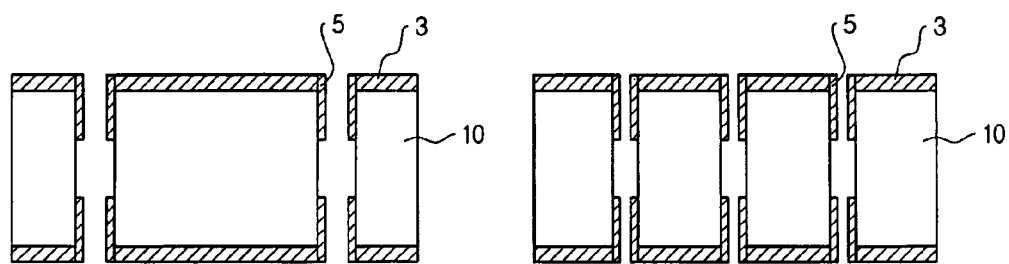

After determining the thickness of the micro spike, a vapor deposition process of covering a passivation film 5 is performed as shown in FIG. 12C. The passivation film 5 is provided so that outer and inner surfaces of each extension part of the micro spike are not etched in a subsequent etching step of the silicon substrate 10. An insulation film such as a silicon oxide film and a silicon nitride film, etc. may be used as a material of the passivation film 5. After that, the reactive ion etching is further performed to define a sacrificial layer to be wet-etched.

Figure 12D:
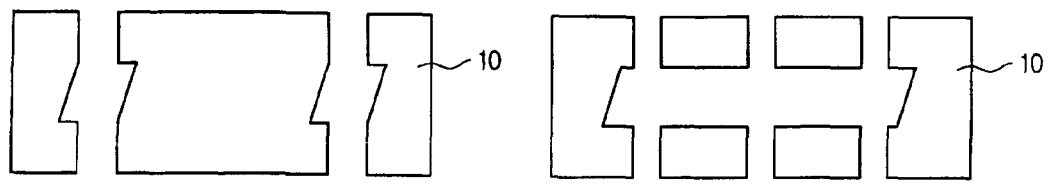

After defining the sacrificial layer as described above, an anisotropic wet etching using an alkaline solution is performed and then a dicing process is performed as shown in FIG. 12D, thereby separating the three-dimensional micro spike from the silicon substrate 10.

Like this, the micro spike of the invention has a durability superior to a structure according to the prior another method since it is made of single crystalline silicon, and it is possible to manufacture a micro spike having a precise shape because it is manufactured using the both surfaces SBM micro processing method. Meanwhile, in order to improve bio-compatibility and strength of the micro spike manufactured as described above, the surface of the micro spike can be coated with a bio-compatible organic thin film such as a parylene thin film, a polymer film, a silicon oxide film, a silicon nitride film, gold or aluminum.

The three-dimensional micro spike manufactured as such can pick more amounts of tissue than the biopsy tool having a two-dimensional structure such as a micro needle of the prior art, and the three-dimensional structure itself can serve as a storage of the picked tissue. Like this, since the micro spike of the invention can be made to be micro using a silicon micro machining process, it is possible to miniaturize the biopsy tool, to perform a micro biopsy on the tissue, and to minimize an invasion of the biopsy tool for a patient.

As described above, according to the invention, it is possible to pick an enough amount of the tissue to examine the tissue just by inserting and extracting the micro spike into and from the tissue region, to prevent a perforation with minimal invasion and to minimize an examinee's pain in picking the tissue.

In addition, according to the invention, the sacrificial bulk micromachining (SBM) processing method is applied to the single crystalline silicon substrate, so that it is possible to easily manufacture a three-dimensional micro spike having a firm structure. Further, a micro spike according to the invention is not costly to manufacture and thus may be used as a disposable item.

While the invention has been shown and described with reference to certain preferred embodiments thereof, it will be understood by those skilled in the art that various changes in form and details may be made therein without departing from the spirit and scope of the invention as defined by the appended claims.

What is claimed is:

1. A micro spike comprising:
   a main body part capable of being mounted on a medical device and configured for insertion into a patient body along with said medical device for sampling a tissue sample from an organ in the patient body;
   at least four extension parts configured for insertion into the tissue of the organ in the patient body for sampling the tissue sample and are integrally extended toward the direction of the patient body in which the main body part is inserted, and are extensions on the upper, lower, left and right parts of one side of the main body part; and
   protrusion parts integrally protruded from side surfaces of the extension parts which are opposite to each other and configured for insertion into the tissue to sample the tissue sample together with the extension parts for sampling the tissue sample;
   wherein the width between said extension parts (t) is narrower than the width of said main body part (x),
   wherein the protrusion parts are not formed on the outer side surfaces of the extension part on the left-most part and the extension part on the right-most part, and are inclined toward an opposite direction from a direction spiking the patient body so that an angle between the protrusion part and the extension part is an acute angle, wherein at least one of the protrusion parts are formed on the side surfaces of each extension part to face each other.

2. The micro spike according to claim 1, wherein a shape of the protrusion part is a wing shape.

3. The micro spike according to claim 1, wherein the protrusion part has a width (W) between 5 micrometer and 5 millimeter, a space (D) between 5 micrometer and 5 millimeter, and a height (H) between 5 micrometer and 5 millimeter.

4. The micro spike according to claim 1, wherein a surface of the micro spike is coated with any one of parylene, polymer film, a silicon oxide film, a silicon nitride film, gold and aluminum.

5. The micro spike according to claim 1, wherein the number of the extension part respectively formed at the upper and lower parts of the one side of the main body is between 2 and 10.

6. The micro spike according to claim 1, wherein the micro spike comprises a single crystalline silicon.

7. The micro spike according to claim 1, wherein the main body part comprises a connection means to connect the main body part to the medical device.

8. The micro spike according to claim 1, wherein the micro spike is capable of being connected or separated to or from the medical device by inserting the main body part into a recess formed in the medical device or extracting the main body part from the recess after the insertion.

9. The micro spike according to claim 1, wherein the main body part comprises at least a recess to connect the main body part to the medical device.

10. The micro spike according to claim 1, wherein at least an extension parts are further formed between the extension part from the left part and the extension part from the right part on the one side of the main body part.

11. The micro spike according to claim 1, wherein the extension part has a length between 1.5 millimeter and 15 millimeter.

12. The micro spike according to claim 11, wherein the extension part has a length between 2 millimeter and 10 millimeter.

13. The micro spike according to claim 1, wherein the width and the length of the main body part is respectively within a range between 100 micrometer and 50 millimeter, and the thickness of the main body part is within a range between 100 micrometer and 10 millimeter.

14. The micro spike according to claim 13, wherein the width and the length of the main body part is respectively within a range between 500 micrometer and 5 millimeter, and the thickness of the main body part is within a range between 200 micrometer and 2 millimeter.

15. The micro spike according to claim 10, wherein protrusion parts are formed on both side surfaces of the extension part which is formed between the extension part from the left part and the extension part from the right part on the one side of the main body part.

16. The micro spike according to claim 3, wherein the protrusion part has a width (W) between 50 micrometer and 1 millimeter, a space (D) between 50 micrometer and 1 millimeter, and a height (H) between 50 micrometer and 1 millimeter.

17. A micro spike comprising:
- a main body part capable of being mounted on a medical device and configured for insertion into a patient body along with said medical device for sampling a tissue sample from an organ in the patient body;
- at least two pairs of extension parts configured for insertion into the tissue of the organ in the patient body for sampling the tissue sample and integrally extended toward the direction of the patient body in which the main body part is inserted, and are extensions on the upper and lower parts of one side of the main body part, wherein a pair of extension parts consists of two extension parts, one of which is extended from the left part of the one side of the main body part, and the other of which is extended from the right part of the one side of the main body part; and
- protrusion parts integrally protruded from opposing side surfaces of each of the pair of the extension parts and configured for insertion into the tissue to sample the tissue sample together with the extension parts for sampling the tissue sample,
- wherein the width between said pair of extension part (t) is narrower than the width of said main body (x),
- wherein the protrusion part is not formed on the outer side surfaces of the extension part on the left-most part and the extension part on the right-most part, and are inclined toward an opposite direction from a direction spiking the patient body so that an angle between the protrusion part and the extension part is an acute angle, wherein at least one of the protrusion parts are formed on the side surfaces of each extension part to face each other.

18. The micro spike according to claim 17, wherein a shape of the protrusion part is a wing shape.

19. The micro spike according to claim 17, wherein the protrusion part has a width (W) between 5 micrometer and 5 millimeter, a space (D) between 5 micrometer and 5 millimeter, and a height (H) between 5 micrometer and 5 millimeter.

20. The micro spike according to claim 17, wherein a surface of the micro spike is coated with any one of parylene, polymer film, a silicon oxide film, a silicon nitride film, gold and aluminum.

21. The micro spike according to claim 17, wherein the number of the pairs of the extension parts formed at the upper and lower parts of the one side of the main body part is between 2 and 10.

22. The micro spike according to claim 17, wherein the micro spike is capable of being connected or separated to or from the medical device by inserting the main body part into a recess formed in the medical device or extracting the main body part from the recess after the insertion.

23. The micro spike according to claim 17, wherein the micro spike comprises a single crystalline silicon.

24. The micro spike according to claim 17, wherein the main body part comprises a connection means to connect the main body part to the medical device.

25. The micro spike according to claim 17, wherein the width and the length of the main body part is respectively within a range between 100 micrometer and 50 millimeter, and the thickness of the main body part is within a range between 100 micrometer and 10 millimeter.

* * * * *